(12) United States Patent
Dirkzwager et al.

(10) Patent No.: US 6,437,207 B1
(45) Date of Patent: Aug. 20, 2002

(54) PROCESS FOR THE PREPARATION OF STYRENES

(75) Inventors: Hendrik Dirkzwager; Marinus Van Zwienen, both of Amsterdam (NL)

(73) Assignee: Shell Oil Company, Houston, TX (US)

( * ) Notice: Subject to any disclaimer, the term of this patent is extended or adjusted under 35 U.S.C. 154(b) by 0 days.

(21) Appl. No.: 09/700,302

(22) PCT Filed: Apr. 27, 1999

(86) PCT No.: PCT/EP99/03018

§ 371 (c)(1),
(2), (4) Date: Nov. 9, 2000

(87) PCT Pub. No.: WO99/58480

PCT Pub. Date: Nov. 18, 1999

(30) Foreign Application Priority Data

May 11, 1998 (EP) .......................................... 98201527

(51) Int. Cl.$^7$ ............................ C07C 1/207; C07C 1/20
(52) U.S. Cl. ...................................... 585/437; 585/436
(58) Field of Search ................................. 585/436, 437

(56) References Cited

U.S. PATENT DOCUMENTS 3,526,674 A  *  9/1970  Becker et al. .............. 585/437

* cited by examiner

Primary Examiner—Thuan D. Dang
(74) Attorney, Agent, or Firm—Y. Grace Tsang

(57) ABSTRACT

Process for the preparation of styrene comprising the gas phase dehydration of 1-phenyl-ethanol at elevated temperature in the presence of a dehydration catalyst, wherein the dehydration catalyst consists of shaped alumina catalyst particles having a surface area (BET) in the range of from 80 to 140 m$^2$/g and a pore volume (Hg) in the range of from 0.35 to 0.65 ml/g, of which 0.03 to 0.15 ml/g is in pores having a diameter of at least 1000 nm.

7 Claims, No Drawings

PROCESS FOR THE PREPARATION OF STYRENES

The present invention relates to a process for the preparation of styrene or substituted styrenes from a feed containing 1-phenyl-ethanol (also known as α-phenyl-ethanol or methyl-phenyl-carbinol) or substituted 1-phenyl-ethanol in the presence of a specific alumina-based dehydration catalyst.

A commonly known method for manufacturing styrene is the coproduction of propylene oxide and styrene starting from ethylbenzene. In general such process involves the steps of (i) reacting ethylbenzene with oxygen or air to form ethylbenzene hydroperoxide, (ii) reacting the ethylbenzene hydroperoxide thus obtained with propene in the presence of an epoxidation catalyst to yield propylene oxide and 1-phenyl-ethanol, and (iii) converting the 1-phenyl-ethanol into styrene by dehydration using a suitable dehydration catalyst. The present invention particularly focuses on the last step, i.e. the dehydration of 1-phenyl-ethanol to yield styrene.

Within the further context of the present application the term "styrene" also embraces substituted styrenes, by which are meant styrenes containing one or more substituents bonded to the aromatic ring or to the vinyl group. Such substituents typically include alkyl groups, such as methyl or ethyl groups. Similarly, the term "1-phenyl-ethanol" also embraces substituted 1-phenyl-ethanols having the same substituents as the corresponding substituted styrenes.

The production of styrene by dehydrating 1-phenyl-ethanol is well known in the art. It can be carried out both in the gas phase and in the liquid phase. Suitable heterogeneous dehydration catalysts for use in both liquid phase and gas phase dehydration include, for instance, acidic materials like alumina, alkali alumina, aluminium silicates and H-type synthetic zeolites. An example of a suitable homogeneous catalyst for use in a liquid phase dehydration process is p-toluene-sulphonic acid. Dehydration conditions are also well known and usually include reaction temperatures of 100–300° C. for liquid phase dehydration and 210–330° C. for gas phase dehydration. Pressures usually range from 0.1 to 10 bar.

The present invention focuses on the use of specific, shaped alumina catalysts for use in the gas phase dehydration of 1-phenyl-ethanol into styrene. As indicated above, the use of alumina catalysts in the dehydration of 1-phenyl-ethanol is well known in the art.

For instance, U.S. Pat. No. 3,526,674 discloses the use of an alumina catalyst in the liquid phase dehydration of 1-phenyl-ethanol into styrene, wherein said alumina catalyst suitably has a BET surface area of 40 to 250 m$^2$/g and is used in finely divided form, i.e. in the form of particles having a particle size of about 0.15 mm (100 mesh) or less.

U.S. Pat. No. 3,658,928 discloses a process for the gas phase dehydration of 1-phenyl-ethanol into styrene in the presence of controlled amounts of added steam and in the presence of a catalyst, which suitably is a commercially available alumina catalyst like Harshaw Al-0104. Table IV shows that the specific surface area of the fresh alumina catalyst employed is 109 m$^2$/g.

In general, a gas phase dehydration process is carried out by passing the feed gas through a fixed bed of catalyst particles. The packing of the catalyst bed is important. Namely, the use of small catalyst particles on the one hand implies a high contact surface and hence a high conversion level, but on the other hand small particles mean a dense packing and hence a high pressure drop. It is therefore important to find the right balance between conversion level and pressure drop.

The present invention aims to provide a process for producing styrene by the gas phase dehydration of 1-phenyl-ethanol, wherein styrene is obtained at improved selectivity and at high yield. Furthermore, the dehydration catalyst used should have sufficient mechanical stability and should minimise pressure drop across the reactor. An optimum balance between conversion level and pressure drop, accordingly, is aimed at.

These aims have been achieved by using a shaped alumina catalyst having specific characteristics including a certain amount of macroporosity.

Accordingly, the present invention relates to a process for the preparation of styrene comprising the gas phase dehydration of 1-phenyl-ethanol at elevated temperature in the presence of a dehydration catalyst, wherein the dehydration catalyst consists of shaped alumina catalyst particles having a surface area (BET) in the range of from 80 to 140 m$^2$/g and a pore volume (Hg) in the range of from 0.35 to 0.65 ml/g, of which 0.03 to 0.15 ml/g is in pores having a diameter of at least 1000 nm.

The term "alumina" as used in connection with the present invention refers to an inorganic oxide consisting for at least 90% by weight (wt %), preferably at least 95 wt % and most preferably at least 99 wt %, of Al$_2$O$_3$. The remainder up to 100 wt % may consist of minor amounts of other inorganic oxides like SiO$_2$ and alkali metal oxides. Suitable aluminas include γ-alumina, δ-alumina, ρ-alumina and θ-alumina, of which the use of γ-alumina is preferred.

The expression "shaped alumina catalyst" refers to a catalyst consisting of alumina particles having a certain spatial shape. Suitably such catalyst particles can be obtained by a method involving extrusion and calcination, wherein the spatial shape of the particles is obtained by using an extruder having a dieplate with an orifice of the desired shape.

The shaped alumina catalyst to be used in the process of the present invention has a surface area in the range of from 80 to 140 m$^2$/g. The surface area is determined according to the well known Brunauer-Emmett-Teller (BET) method. Preferably, the surface area of the catalyst used is in the range of 85 to 115 m$^2$/g.

The pore volume of the shaped alumina catalyst has a value in the range of from 0.35 to 0.65 ml/g, 0.03 to 0.15 ml/g of which is in pores having a diameter of at least 1000 nm, and is determined according to the well known mercury porosimetry. Preferably, the pore volume (Hg) is in the range of from 0.40 to 0.60 ml/g, of which 0.05 to 0.12 ml/g is in pores having a diameter of at least 1000 nm. The pores having a diameter of 1000 nm or more are also referred to as macropores. The presence of a certain level of macroporosity in the shaped alumina catalyst used in the process according to the present invention has been found to be very advantageous.

The diameter of the catalyst particles is not particularly critical to the present invention. Diameters normally used for this kind of catalysts may be employed. The term "diameter" as used in this connection refers to the largest distance between two opposite points on the perimeter of the cross-section of a catalyst particle. In case of rod-like particles having a shaped cross-section, this shaped cross-section is the relevant cross-section. It has been found particularly advantageous for the purpose of the present invention to use catalyst particles having a diameter of 1.5 to 8 mm, preferably 2.5 to 4.5 mm.

The catalyst particles may have any shape, including spherical, cylindrical, trilobal, quadrulobal, star-shaped, ring-shaped, cross-shaped etc. It has, however, been found particularly preferred to use a star-shaped catalyst, i.e. rod-like catalyst particles having a star-shaped cross-section. The star may have any desirable number of corners, but a four- five- or six-cornered star-shape is preferred. It has been found particularly preferred to use star-shaped catalyst particles having a (average) length/diameter ratio of the catalyst particles has a value in the range of from 0.5 to 3, preferably from 1.0 to 2.0. The "length" in this connection refers to the length of the rod.

The catalyst particles to be used suitably have a bulk density which allows an effective packing of the reactor in a fixed bed operation, but without causing a too high a pressure drop. In this respect it has been found beneficial to use catalyst particles which have a bulk density of at least 0.5 g/ml, preferably in the range of from 0.6 to 1.5 g/ml.

The catalyst particles should also have sufficient mechanical strength. One of the advantages of the present invention is that the specific catalyst particles to be used have a very good mechanical strength, both in terms of side crushing strength (SCS) and bulk crushing strength (BCS), whilst at the same time possessing macroporosity. Accordingly, the catalyst particles used have a SCS of at least 20 N, preferably at least 40 N, and a BCS of at least 0.8 MPa, suitably 1.0 to 2.5 MPa.

The dehydration of 1-phenyl-ethanol into styrene according to the present invention is carried out in the gas phase. The dehydration conditions to be applied are those normally applied and include reaction temperatures of 210–330° C., suitably 280–320° C., and pressures in the range of from 0.1 to 10 bar.

In the process according to the present invention the catalyst described herein before has a reaction selectivity to styrene of at least 95% as well as an activity of at least 95%, whilst selectivities of 99% or higher and activities of 97% and higher have been achieved. In this connection reaction selectivity is defined as the number of moles styrene formed per mole of 1-phenyl-ethanol that is converted. Activity is defined as the overall conversion level of 1-phenyl-ethanol as determined under test conditions, i.e. the mole percentage of 1-phenyl-ethanol converted relative to the total number of moles of 1-phenyl-ethanol present in the feed.

The invention will now be illustrated by the following examples without limiting the scope of the invention to these particular embodiments. In these examples the surface area is determined according to the BET-method and the pore volume with mercury porosimetry.

Example 1

A star-shaped catalyst having the physical properties as indicated in Table I (Ex-1) was tested for dehydration performance in a microflow unit consisting of a 13 mm diameter plugflow reactor, 1-phenyl-ethanol feed facilities and product vapour condensing facilities. As 1-phenyl-ethanol feedstock was used a sample of the process stream to the Styrene reactor system of the commercial Propylene Oxide/Styrene Monomer plant. The feedstock contained 79.8% 1-phenyl-ethanol, 11.1% methyl-phenyl-ketone and 1.8% water. The remainder up to 100% consisted of impurities and (by)products of the preceding epoxidation section. The outlet stream of the micro flow unit was liquefied by condensation and the resulting two phase liquid system was analysed by means of Gaschromatographic analysis.

The dehydration experiment was carried out at standard test conditions of 1.0 bara pressure and a temperature of 300° C. The feed rate of 1-phenyl-ethanol was maintained at 30 grams per hour and the reactor tube was loaded with 20 cm$^3$ catalyst, which corresponds to 13.8 grams of star-shaped catalyst particles having a length/diameter ratio of about 1.1. The reaction was continued for approximately 90 hours after which the experiment was stopped.

Activity and reaction selectivity of the star-shaped catalyst were determined from the Gaschromatographic analyses of reaction product samples collected between runhour 17 and runhour 30.

The results are indicated in Table I.

COMPARATIVE EXAMPLE 1

Example 1 was repeated except that the microflow reactor tube was loaded with 20 grams (20 cm$^3$) of commercially available Aluminium Oxide 0.32 cm (⅛") Tablets (Al-0104 ex Engelhard De Meern B.V.), which may suitably be applied in 1-phenyl-ethanol dehydration reaction. Physical properties of the catalyst tablets are indicated in Table I (CEx-1).

Activity and reaction selectivity of the catalyst tablets were determined from the Gaschromatographic analyses of reaction product samples collected between runhour 19 and runhour 27.

The results are indicated in Table I.

COMPARATIVE EXAMPLE 2

Example 1 was repeated except that the microflow reactor tube was loaded with 13.6 grams (20 cm$^3$) of star-shaped Aluminium Oxide catalyst particles, which are essentially free of any macropores (pores having a diameter above 1000 nm). Physical properties of the catalyst particles are indicated in Table I (CEx-2).

Activity and reaction selectivity of the catalyst were determined from the Gaschromatographic analyses of reaction product samples collected between runhour 14 and runhour 27.

The results are indicated in Table I.

From Table I it can be seen that catalyst used in the process according to the present invention has very good mechanical properties in combination with excellent activity and selectivity.

TABLE I

Catalyst properties and performance

|  | Ex-1 | CEx-1 | CEx-2 |
|---|---|---|---|
| Shape | star | tablet | star |
| Surface area (m$^2$/g) | 99 | 102 | 111 |
| Pore Volume (ml/g) | 0.57 | 0.35 | 0.45 |
| Pore Volume >1000 mm (ml/g) | 0.07 | 0.02 | nil |
| Side Crushing Strength (N) | 61 | 44.2 | 50 |
| Bulk Crushing Strength (MPa) | 1.1 | >1.6 | 1.1 |
| Bulk density (ml/g) | 0.71 | 1.0 | 0.69 |
| Particle diameter (mm) | 3.6 | 3.2 | 3.5 |
| Activity (%) | 97.82 | 95.97 | 97.36 |
| Reaction selectivity (%) | 98.35 | 96.16 | 97.04 |

What is claimed is:

1. A process for preparing styrene, which process comprises a step of:
   dehydrating 1-phenyl-ethanol under gas phase at elevated temperature in the presence of a dehydration catalyst to produce styrene,
   wherein the dehydration catalyst comprises shaped alumina catalyst particles having a surface area (BET) in the range of from 80 to 140 m$^2$/g and a pore volume (Hg) in the range of from 0.35 to 0.65 ml/g, of which 0.03 to 0.15 ml/g is in pores having a diameter of at least 1000 nm.

2. The process according to claim 1, wherein the surface area is in the range of 85 to 115 $m^2/g$.

3. The process according to claim 1, wherein the pore volume (Hg) is in the range of from 0.40 to 0.60 ml/g, of which 0.05 to 0.12 ml/g is in pores having a diameter of at least 1000 nm.

4. The process according to claim 1, wherein the catalyst particles have a diameter of 1.5 to 8 mm.

5. The process according to claim 1, wherein the catalyst particles are star-shaped.

6. The process according to claim 5, wherein the catalyst particles have a length/diameter ratio in the range of from 0.5 to 3.0.

7. A process according to claim 1, wherein the catalyst particles have a bulk density in the range of from 0.6 to 1.5 g/ml.

* * * * *